United States Patent [19]
Barton et al.

[11] Patent Number: 6,071,707
[45] Date of Patent: Jun. 6, 2000

[54] PHOSPHOTYROSINE MIMICS AND METHOD FOR IDENTIFYING AND USING SAME

[75] Inventors: Randall W. Barton, Farmington; Charles A. Kennedy, Southbury, both of Conn.

[73] Assignee: Boehringer Ingelheim Pharmaceuticals, Inc., Ridgefield, Conn.

[21] Appl. No.: 08/852,042

[22] Filed: May 6, 1997

Related U.S. Application Data

[60] Provisional application No. 60/016,322, May 7, 1996.
[51] Int. Cl.[7] .......................... G01N 33/53; A61K 38/16; C07K 16/00
[52] U.S. Cl. .......................... 435/7.1; 435/7.94; 530/352; 530/388.26; 424/146.1
[58] Field of Search ..................... 435/7.94, 7.1; 530/352, 388.26; 424/146.1; 514/19; 562/545

[56] References Cited

U.S. PATENT DOCUMENTS 5,834,434 11/1998 Sebti et al. ................................ 514/19

OTHER PUBLICATIONS

Houghten et al., BioFeature., vol. 13., No. 3., pp. 412–421., 1992.
Gordon et al., Journal of medicinal chemistry., vol. 37., No. 10., pp. 1385–1401, May 1994.
Bin Ye et al., J. Med. Chem., vol. 38., No. 21., pp. 4270–4275., 1995.
Ruff–Jamison et al., J. Biol. Chem., 1991., vol. 266., No. 10., pp. 6607–6613., 1991.

*Primary Examiner*—Keith D MacMillan
*Assistant Examiner*—P. Ponnaluri
*Attorney, Agent, or Firm*—Robert P. Raymond; Alan R. Stempel; Mary-Allen M. Devlin

[57] ABSTRACT

This invention relates to phosphotyrosine mimics which, when incorporated into an appropriate molecular structure, are capable of inhibiting the binding of tyrosine kinase-dependent regulatory proteins to the native phosphotyrosine-containing receptors. This invention also relates to methods and kits for identifying and using phosphotyrosine mimics. The compounds, kits and methods of this invention are useful for identifying and designing antagonists of tyrosine-kinase dependent regulatory proteins, such as signal transduction proteins containing $SH_2$ binding domains.

7 Claims, No Drawings

PHOSPHOTYROSINE MIMICS AND METHOD FOR IDENTIFYING AND USING SAME

RELATED APPLICATIONS

The benefit of prior provisional application Ser. No. 60/016,322 filed on May 7, 1996, is hereby claimed.

TECHNICAL FIELD OF INVENTION

This invention relates to phosphotyrosine mimics which, when incorporated into an appropriate molecular structure, are capable of inhibiting the binding of tyrosine kinase-dependent regulatory proteins to their native phosphotyrosine-containing ligands or receptors. This invention also relates to methods and kits for identifying and using phosphotyrosine mimics. The compounds, kits and methods of this invention are useful for identifying and designing antagonists of tyrosine-kinase dependent regulatory proteins, such as signal transduction proteins containing $SH_2$ binding domains.

BACKGROUND OF THE INVENTION

The activation of cells by growth factors, mitogens or other cytokines to undergo proliferation and/or differentiation is often dependent on inducible tyrosine kinase activity. This tyrosine kinase activity increases the phosphotyrosine content of many receptor-like and cytoplasmic regulatory proteins. Often, the physical association of such regulatory proteins is mediated through those phosphotyrosine residues.

For example, one mechanism of cellular regulation involves the physical association of signal transduction proteins with one or more phosphorylated tyrosine-containing receptor subunits, called immunoreceptor tyrosine-based activation motifs (ITAMs), present on its native ligand or receptor. This association is a common feature of many cytoplasmic signal transduction pathways, as well as other immunologically important regulatory protein-receptor based interactions (M. A. Osborne et al., BioTechnology, 13 (1995)). Of particular importance is the interaction between phosphorylated ITAMs and regulatory proteins containing Src homology domain 2 regions ("$SH_2$ binding domains"). Examples of immunologically important proteins containing $SH_2$ binding domains include ZAP-70, Fyn, Lyn, Lnk, Abl, Vav, Huk, Blk, PLCγγl, GAP, Crk, Shc and $p^{56}lck$. Although proteins having $SH_2$ binding domains tend to have sequence-specific affinities for their ITAM containing ligands or receptors, the binding interaction itself is ubiquitously mediated through one or more phosphorylated tyrosine residues. Therefore, the presence of phosphorylated tyrosine plays a critical role in signal transduction involving virtually all proteins containing $SH_2$ binding domains.

Given the above understanding of signal transduction and cellular regulation, it follows that growth factor- and cytokine-induced cell proliferation and/or differentiation can be selectively inhibited by antagonizing the interaction of regulatory proteins dependent on tyrosine kinase activity with their native phosphotyrosine-containing ligands or receptors. Such antagonists would undoubtedly be useful to treat a variety of disorders, including those associated with or caused by neoplastic diseases or chronic inflammatory diseases.

To date, however, antagonists of tyrosine kinase-dependent regulatory proteins have not fulfilled their potential as useful pharmaceutical agents. One major hurdle has been the necessary inclusion of a phosphorylated α-amino acid residue or a phosphorylated analog thereof, to perform the crucial role of the native tyrosine phosphoprotein ligands or receptors of these regulatory proteins. However, agents containing phosphotyrosine, other phosphorylated α-amino acid residues, or phosphorylated analogs thereof, cannot generally be used as therapeutic agents because the presence of the phosphorylated moiety substantially impedes cell penetrability. Until now, no effective replacement or mimic for the critical phosphotyrosine residue has been identified. Further, no accurate methods for identifying such phosphotyrosine mimics have existed. Accordingly, the need exists for effective phosphotyrosine mimics and convenient methods for identifying such mimics.

BRIEF DESCRIPTION OF THE INVENTION

This invention satisfies the above-mentioned needs by providing phosphotyrosine mimics and convenient methods for identifying phosphotyrosine mimics.

One object of this invention is to provide a method for identifying phosphotyrosine mimics comprising the steps of:

(a) contacting a non-phosphorylated test compound and a phosphotyrosine-containing substance with an anti-phosphotyrosine antibody; and (b) detecting the ability of the non-phosphorylated test compound to bind to the anti-phosphotyrosine antibody.

Another object of this invention is to provide phosphotyrosine mimics that, when incorporated into an appropriate molecular structure, inhibit the binding of tyrosine kinase-dependent regulatory proteins to their native phosphotyrosine-containing ligands or receptors.

Yet another object of this invention is to provide kits for determining the presence of a phosphotyrosine mimic in a non-phosphorylated test compound.

A further object of this invention is to provide methods for using phosphotyrosine mimics to inhibit the activation of tyrosine kinase-dependent regulatory proteins.

Yet a further object of this invention is to provide a method for treating neoplastic or chronic inflammatory disease using the phosphotyrosine-containing compounds according to this invention.

Other objects and advantages of this invention will be apparent to those of ordinary skill in the art.

DETAILED DESCRIPTION OF THE INVENTION

Unless otherwise indicated, the following definitions apply:

The terms "amino acid" and "α-amino acid" are used interchangeably herein and refer to the naturally occurring α-amino acids, as well as those amino acids in their D-configurations and non-native, synthetic and modified amino acids known to those of ordinary skill in the art (e.g., homocysteine, ornithine, norleucine and β-valine).

The term "patient" refers to a warm-blooded animal, such as a human, who is afflicted with a neoplastic or chronic inflammatory disorder.

The term "phosphotyrosine mimic" refers to a non-phosphorylated chemical moiety which is functionally capable of replacing phosphotyrosine in a native phosphotyrosine-containing ligand. Specifically, when incorporated into an appropriate molecular structure, a phosphotyrosine mimic is capable of antagonizing the binding of a tyrosine kinase dependent regulatory protein to its natural ligand(s). The antagonistic ability of such compounds may be detected by any of the detection methods described herein, or any other conventional detection method known to those of ordinary skill in the art. Preferably, a phosphotyrosine mimic-containing compound according to this invention is capable of inhibiting the binding of a tyrosine kinase-dependent regulatory protein to its corresponding, phosphorylated ligand or receptor by at least about 30% at a concentration of 10 $\mu$M (more preferably, by at least about 35%, even more preferably, by at least about 40%, even more preferably, by at least about 50% and most preferably, by at least 60%, 70% or even 80%).

Preferred phosphotyrosine mimic-containing compounds according to this invention are characterized by improved cell penetrability over that possessed by the corresponding phosphotyrosine-containing analogs. The improved cell penetrability possessed by these compounds advantageously allows the compounds to more readily pass through the cell membrane, thereby increasing the likelihood of physical interaction with the targeted regulatory protein (such as a particular targeted phosphotyrosine kinase-dependent regulatory protein containing an $SH_2$ binding domain).

The present invention also provides a convenient and sensitive method for identifying phosphotyrosine mimics by utilizing anti-phosphotyrosine antibodies to rapidly screen large numbers of non-phosphorylated test compounds. Specifically, this method comprises the steps of:

(a) contacting a non-phosphorylated test compound and a phosphotyrosine-containing substance with an anti-phosphotyrosine antibody; and (b) detecting the ability of the non-phosphorylated test compound to inhibit the binding of the anti-phosphotyrosine antibody to the phosphotyrosine-containing substance.

In a preferred embodiment, the method for identifying a phosphotyrosine mimic according to this invention comprises the steps of:

(a) competitively binding a non-phosphorylated test compound and a phosphotyrosine-containing substance with an anti-phosphotyrosine antibody; and (b) detecting the degree to which the non-phosphorylated test compound displaces the phosphotyrosine-containing substance.

More preferably, the method for identifying a phosphotyrosine mimic according to this invention comprises the steps of:

(a) incubating a non-phosphorylated test compound with an anti-phosphotyrosine antibody to form a solution;

(b) contacting the solution of step (a) with a known amount of a phosphotyrosine-containing substance; and (c) detecting the degree to which the non-phosphorylated test compound displaces the phosphotyrosine-containing substance.

In each of the above embodiments, preferred non-phosphorylated test compounds containing a phosphotyrosine mimic according to this invention are capable of inhibiting the binding of the anti-phosphotyrosine antibody to the phosphotyrosine-containing substance by at least about 30% at a concentration of 10 $\mu$M (more preferably, by at least about 35%, even more preferably, by at least about 40%, even more preferably, by at least about 50% and most preferably, by at least 60%, 70% or 80%).

The anti-phosphotyrosine antibodies useful in the methods of this invention are those which are capable of binding to a phosphotyrosine residue present in a phosphotyrosine-containing compound, wherein the phosphotyrosine residue is free of steric hindrance or other blockage to reaction with the antibody. Such anti-phosphotyrosine antibodies are well known to those of ordinary skill in the art and may be easily obtained by in-vivo production and harvesting according to known techniques. In general, conventional techniques for producing and harvesting monoclonal anti-phosphotyrosine antibodies comprise injecting a mammal (e.g. a mouse) with a compound containing a phosphotyrosine residue, fusing the mammal's spleen cells with myeloma cells and assaying the resultant hybridoma cells for antibodies which specifically bind to phosphotyrosine residues in different phosphotyrosine-containing proteins containing phosphotyrosine. Once identified, the cells producing these antibodies can be cloned and grown in mass culture or injected into an animal (e.g., a mouse) to induce secretion of the desired antibody. As those of ordinary skill in the art will readily appreciate, other conventional methods for producing anti-phosphotyrosine antibodies may be used equally well for the purposes of this invention.

Alternatively, anti-phosphotyrosine antibodies may be purchased commercially (for example, PY-20, 4G10, B4, RC20, 1G2, 25.2G4, 3-365-10, 6D12, PT66, PY54, PY69 and Z027 are available from suppliers such as Transduction Labs (Lexington, Ky.), Zymed (South San Francisco, Calif.), Upstate Biotechnology (Lake Placid, N.Y.), Biogenesis LTD (Sandown, N.H.), Boehringer Mannheim Biochemicals (Indianapolis, Ind.), Wako Chemicals USA Inc (Richmond, Va.), Medical & Biological Labs LTD (Nagoya, Japan), Sigma Chemical Co (St Louis Mo.), Biodesign International (Kennebunk Me.), and ICN Biochemicals (Costa Mesa, Calif.). Although the methods of this invention envision use of any suitable anti-phosphotyrosine antibody (e.g., polyclonal or monoclonal; human or non-human), preferably the antibody is a commercially available, monoclonal antibody which specifically and selectively targets the phosphotyrosine residue of one or more naturally occurring phosphotyrosine-containing ligands. More preferably, the antibody is a mouse anti-phosphotyrosine monoclonal antibody. Most preferably the antibody is PY-20.

The methods of this invention employ assays which measure anti-phosphotyrosine antibody binding affinity of a non-phosphorylated test compound versus a phosphotyrosine-containing substance. Although all assays that perform this function are contemplated by this invention, direct binding assays are less preferred because they tend to be difficult to carry out in a high-throughput manner. Competitive binding assays are preferred because they are more easily and quickly performed with a large number of non-phosphorylated test compounds. Many such competitive binding assays are well known to those of ordinary skill in the art. Competitive binding assays which may be used in the methods of this invention are typically immunoassays that detect the presence or concentration of the free or bound forms of anti-phosphotyrosine antibody, phosphotyrosine-containing substance or non-phosphorylated test compound. Depending on precisely which immunoassay is used, the free- and bound-forms of those substances may be readily distinguished using an appropriate label.

Typically, the known phosphotyrosine-containing substance or the anti-phosphotyrosine antibody for use in the methods of this invention is conjugated with a conventional monitorable label which does not interfere with the ability of the known phosphotyrosine-containing substance and the anti-phosphotyrosine antibody to cross-react. Labels that are generally useful for this purpose include, but are not limited to, chemical ligands, enzymatic labels, radioactive labels, fluorescent labels, luminescent labels and electronic labels. One particularly useful chemical ligand is biotin. Particularly useful enzymatic labels include, but are not limited to, horseradish peroxidase, β-galactosidase, alkaline phosphatase and acetylcholinesterase. Particularly useful radioactive ligands include, but are not limited to, phosphorus $^{32}$P and $^{33}$P, iodine $^{125}$I and $^{131}$I and hydrogen, $^{3}$H. Particularly useful fluorescent labels include, but are not limited to, rhodamine, tetramethyl rhodamine isothiocyanate, phycoerythrin and dansyl chloride. One particularly useful luminescent label is luminol.

Particularly preferred competitive binding immunoassays useful in the methods of this invention include, but are not limited to, enzyme-linked, fluorescent, chemiluminescent, radio and biosensor immunoassays. Although the immunoassays of this invention may be carried out in solution or on a solid support, we prefer using a solid support (such as the wells of a microtiter plate) to facilitate large-scale screening of non-phosphorylated test compounds. Preferably, the immunoassay used in the methods of this invention is ELISA, a fluorescent immunoassay or a biosensor immunoassay.

In an enzyme-linked immunosorbent assay (ELISA) according to this invention, the known phosphotyrosine-containing substance or the anti-phosphotyrosine antibody may be directly labeled with an enzyme or indirectly labeled with an enzyme-labeled antibody. The enzyme labels useful for ELISA are those that, under appropriate conditions, catalyze an observable reaction with a given enzymatic substrate. Such enzymatic activity is typically measured by formation of a colored or otherwise easily identifiable reaction product. In a typical ELISA scheme according to this invention, the unlabeled compound (either the known phosphotyrosine-containing substance or the anti-phosphotyrosine antibody) is bound to a solid support and the correspondingly labeled substrate is added. After any unbound species are washed away, the non-phosphorylated test compound is added. Unbound species are again removed by washing and the enzyme is activated to determine the extent to which the test compound displaced the known phosphotyrosine-containing substance. Wherever the phosphotyrosine-containing substance was displaced, no enzymatic activity will be detected.

Fluorescent immunoassays useful in the methods of this invention involve the use of conventional fluorochromes. Such fluorochromes may be linked directly to the anti-phosphotyrosine antibody or the known ligand used in the immunoassay, or alternatively, the fluorochrome may be linked indirectly to those compounds with fluorochrome-labeled antibodies. Fluorochromes are dyes that absorb radiation (such as UV light) and emit light of a different characteristic frequency when the labeled compound is bound to a substrate or present in its free state. Therefore, when a known phosphotyrosine-containing substance according to this invention is labeled with a fluorochrome, and the anti-phosphotyrosine antibody and non-phosphorylated test compound are subsequently added, it is a routine matter to detect the extent to which the known phosphotyrosine-containing substance has been displaced by the test compound (e.g., by measuring the amount of free, known phosphotyrosine-containing substance).

In biosensor immunoassays, the binding of an anti-phosphotyrosine antibody to a known phosphotyrosine-containing substance is detected by measuring the change in refractive index that occurs when the solution-phase antibody binds to the known phosphotyrosine-containing substance which has been tethered to an optically sensitive surface. The biosensor allows the determination of equilibrium binding constants together with on and off rates of the interacting molecules. Therefore, when a known phosphotyrosine-containing substance is bound to an optically sensitive surface and the anti-phosphotyrosine antibody and non-phosphorylated test compound are subsequently added, it is a routine matter to detect the extent to which the binding of the anti-phosphotyrosine antibody to the known phosphotyrosine-containing substance has been displaced by the test compound.

This invention also provides a kit for the rapid detection of phosphotyrosine mimics comprising:

(a) an immobilized phosphotyrosine-containing substance and (b) an anti-phosphotyrosine antibody, wherein said antibody is conjugated to a detectable label.

Alternatively, the kit comprises:

(a) an immobilized anti-phosphotyrosine antibody and (b) a phosphotyrosine-containing substance, wherein said substance is conjugated to a detectable label.

Preferred kits are those that comprise the preferred phosphotyrosine-containing substances and preferred anti-phosphotyrosine antibody described above for use in the methods of this invention. The kits of this invention may also include buffers, standards and other conventional reagents to facilitate their use. Preferably, the immobilized component of the kit is covalently bound to a solid resin (such as microtiter plate). Techniques for producing these kits will be readily apparent to those of ordinary skill in the art.

Using the methods and kits of this invention, a panel of non-phosphorylated test compounds may be quickly and efficiently assayed for the presence of a phosphotyrosine mimic. Once identified, these phosphotyrosine mimics may be incorporated into an appropriate molecular structure to provide compounds which inhibit the binding of tyrosine kinase-dependent regulatory proteins to their native receptors. Accordingly, this invention also provides a method for inhibiting the activation of a tyrosine kinase-dependent regulatory protein comprising the steps of:

(a) incorporating a phosphotyrosine mimic according to this invention into an appropriate molecular structure to produce a phosphotyrosine mimic containing compound, and (b) contacting the compound of step (a) with a tyrosine-kinase dependent regulatory protein.

Preferably, the compound of step (a) is covalently attached to a solid support prior to the binding step (b) using known techniques (such as those useful for the kits of this invention).

An example of an appropriate molecular structure for the above detailed use is a phosphotyrosine-containing peptidomimetic in which the phosphotyrosine can be replaced with a phosphotyrosine mimic. Preferably, the peptidomimetic comprises a fragment of a native tyrosine kinase-dependent regulatory protein ligand or receptor, in which the naturally occurring phosphotyrosine residue is replaced with a phosphotyrosine mimic identified by the methods of this invention. Such peptidomimetics generally include from about 1 to about 30 of the naturally occurring α-amino acid residues flanking each side of the naturally occurring phosphotyrosine residue. More preferably, the peptidomimetic comprises from about 1 to about 10 (and most preferably, from about 1 to about 5) of the naturally occurring α-amino acid residues flanking each side of the naturally occurring phosphotyrosine residue. Although the naturally occurring α-amino acids are preferred in these peptidomimetics, those naturally occurring α-amino acids may be optionally modified or substituted according to known techniques. Preferred modifications and substitutions to the naturally occurring amino acid sequence are conservative ones (i.e., those having a minimal influence on the secondary structure and hydropathic nature of the peptide). These include those substitutions and modification described in Dayhoff, *Atlas of Protein Sequence and Structure*, 5 (1978) and Argos, *EMBO J.*, 8, pp. 779–85 (1989).

Peptidomimetics according to this invention may be prepared using known techniques. In general, a phosphotyrosine mimic is used to replace phosphotyrosine in the native peptide sequence by first synthesizing a modified residue containing the phosphotyrosine mimic (having both a carboxy and amino terminus) and using this modified residue to synthesize the peptidomimetic using a known schemes for peptide synthesis.

The above described peptidomimetics may be prepared using any conventional peptide production methodology including solid phase or solution phase synthesis, recombinant DNA technology and combinations thereof. Preferably, these peptidomimetics are produced using solid phase synthesis. The solid support may be any suitable resin conventionally employed in the art. Preferred resins include, but are not limited to p-benzyloxyalcohol polystyrene and p-methylbenzhydrylamine. Amino acids for use in this method may be side chain protected, if necessary. The criteria for choosing an appropriate side chain protecting group include: (a) stability of the side chain protecting group to the reaction conditions needed for removal of the α-amino protecting group, (b) stability of the side chain protecting group to the reaction conditions required for amino acid coupling and (c) removability of the side chain protecting group upon the conclusion of peptide synthesis and under conditions that do not otherwise effect the peptide structure. The first amino acid is amino protected then coupled to the resin. Amino protecting groups include, but are not limited to, 9-fluorenyl-methyloxycarbonyl (FMOC) and t-butoxycarbonyl (BOC). The amino protecting group is then removed using conventional methods. After removal of the amino protecting group, the remaining amino-protected amino acids (side-chain protected, if necessary) are sequentially added to produce the desired peptidomimetic.

The phosphotyrosine mimic identified according to this invention may also be functional group protected, if desired, and added to the growing peptide chain as described above. Functional group protection is well within the ordinary skill of the art and is typically carried out as described above for side group protection. Other protecting groups useful for side chain or functional group protection according to this invention may be found in well known organic chemistry references. It should also be appreciated that phosphotyrosine mimic-containing compounds according to this invention include the free form of such compounds as well as pharmaceutically acceptable salts of those compounds, where such forms exists.

Using the above methodology, phenyl carboxylic acid was identified as a phosphotyrosine mimic according to this invention. Although unsubstituted phenyl carboxylic acid is the preferred phosphotyrosine mimic, this invention also envisions the use of substituted-phenyl analogs of phenyl carboxylic acid (referred to collectively herein as phenyl carboxylic acid mimics). Preferred phenyl substituents include a member of the group consisting of halogens (especially, chloride, fluoride and bromide), branched or unbranched $C_{1-5}$ alkyl, $C_{1-5}$ alkoxy, $C_{2-5}$ alkenyl or alkynyl, (wherein any one of the foregoing alkyl, alkoxy, alkenyl or alkynyl groups may be unsubstituted or substituted with cyano, nitro, amino, trifluoromethyl, trifluoromethoxy or hydroxy and wherein any unsubstituted methylene may be replaced with O, S or C=O), cyano, nitro, amino, trifluoromethyl, trifluoromethoxy and hydroxy. The phenyl carboxylic acid mimic may replace a phosphotyrosine residue in an appropriate molecular structure by attachment at any unsubstituted position on the phenyl ring. Preferably, the phenyl ring is attached to the molecular structure at the 2-position.

The phenyl carboxylic acid mimics according to this invention are structurally simple and advantageously, easily synthesized from commercially available starting materials using conventional synthetic techniques. Similarly, incorporation of a phenyl carboxylic acid mimic into an appropriate molecular structure (and preferably, a peptidomimetic of a native tyrosine kinase-dependent regulatory protein ligand or receptor) is readily accomplished using known techniques and, preferably, the methodology detailed above. Specifically, the phenyl carboxylic acid phosphotyrosine mimic may be used to replace phosphotyrosine in a peptidomimetic by first synthesizing an α-amino acid residue containing the phosphotyrosine mimic (having both a carboxy and amino terminus) and using this modified residue to synthesize the peptidomimetic using any known scheme for peptide synthesis.

It should be understood that only those compounds having combinations of variables that result in stable structures are included within the scope of this invention. Stable structures are those that can be produced according to the above mentioned techniques and stored for an acceptable period of time. Preferably, the stable structures are those that can be stored at 32° F. (0° C.) for at least one week without detectable levels of decomposition. In addition to the free forms of these compounds, this invention also includes the pharmaceutically acceptable salts thereof. The production of pharmaceutically acceptable salts of compounds according to this invention is well within the ordinary skill in the art.

Without wishing to be bound by theory, we believe that the phosphotyrosine mimics according to this invention, when incorporated into an appropriate molecular structure, are capable of binding tyrosine-kinase dependent regulatory proteins in a manner substantially similar or identical to that of the native phosphotyrosine-containing receptor. Therefore, the phosphotyrosine mimic-containing compounds are competitive inhibitors of that binding. Specifically, once bound, the phosphotyrosine mimics inhibit the ability of the regulatory protein to bind its native phosphotyrosine-containing receptor, thereby inhibiting cellular activation. It will be apparent from the nature of this discovery that the immunoassay methods and kits of this invention may be advantageously used to identify phosphotyrosine mimics without reference to a particular tyrosine kinase-dependent regulatory protein. In contrast to mimics that might be identified by competitive binding assays to a specified tyrosine kinase-dependent regulatory protein, the phosphotyrosine mimics identified according to this invention possess a more general utility. By incorporating these mimics into an appropriate molecular structure (as described above), the phosphotyrosine mimics according to this invention may be integrally used as antagonists to virtually any tyrosine kinase-dependent regulatory protein.

As antagonists of tyrosine kinase-dependent regulatory proteins, the phosphotyrosine mimic-containing structures according to this invention can be used to treat a variety of disorders, including those associated with or caused by neoplastic diseases or chronic inflammatory diseases. Specifically, by blocking or displacing the binding of the native phosphotyrosine-containing ligands or receptors of these regulatory proteins, the phosphotyrosine mimic-containing structures according to this invention effectively disrupt the associated regulatory cascades. Representative neoplastic diseases that are treatable with the phosphotyrosine mimic-containing antagonists according to this invention include (but are not limited to): leukemias (including, but not limited to, acute lymphocytic, acute lymphoblastic, chronic lymphocytic, acute myloblastic and chronic mylocytic), carcinomas (including, but not limited to, adenocarcinoma and that of the colon, ovaries, cervix, esophagus, stomach, small intestines, pancreas and lungs), sarcomas (including, but not limited to oesteroma, osteosarcoma, lepoma, liposarcoma, hemangioma, hemangiosarcoma and Karposi's sarcoma), malignant melanomas (including, but not limited to, amelanotic and melanotic), mixed types of neoplasias (such as, but not limited to, carcinosarcoma, lymphoid tissue type, follicular reticulum, cell sarcoma and Hodgkin's disease), neuroblastoma, cerebral malaria, capillary leak syndrome, hematological malignancies and the like. Representative chronic inflammatory diseases treatable with the phosphotyrosine mimic-containing antagonists according to this invention include (but are not limited to): rheumatoid arthritis, multiple sclerosis, Guillain-Barre syndrome, Crohn's disease, ulcerative colitis, psoriasis, graft versus host disease, lupus erythematosus and insulin-dependent diabetes mellitus.

The present invention provides pharmaceutical compositions comprising a therapeutically effective amount of a phosphotyrosine mimic-containing substance according to this invention or, if desired, a pharmaceutically acceptable salt thereof.

The compounds or pharmaceutical compositions according to this invention may be used to treat any of the disease states mentioned above by administering a therapeutically effective amount of a compound or composition according to this invention to a patient. For such treatment, the preferred phosphotyrosine mimic-containing substance is a peptidomimetic of a phosphotyrosine-containing ligand or receptor of a tyrosine-kinase dependent regulatory protein. Preferably, the phosphotyrosine mimic is phenyl carboxylic acid or a functional group protected derivative thereof.

A therapeutically effective amount refers to an amount which is effective, upon single or multiple dose administration to the patient, in controlling the growth of a neoplasm, in alleviating, in whole or in part, the symptoms of the chronic inflammatory disorder, prolonging the survivability or improving the clinical disposition or physical well-being of the patient. Treatment according to this invention may or may not completely eradicate the symptoms or the disorder being treated. A therapeutically effective amount can be readily determined by the attending diagnostician by the use of known techniques and by observing the results obtained under analogous circumstances. In determining a therapeutically effective amount, a number of factors are considered by the attending diagnostician, including (but not limited to): the species of mammal; its size, age and general health; the specific disease involved; the degree of or involvement or the severity of the disease; the response of the individual patient; the particular compound or composition administered; the mode of administration; the bioavailability characteristics of the preparation administered; the dose regimen selected; the use of concomitant mediation and other relevant circumstances.

The compounds and pharmaceutical compositions according to this invention may be administered to the patient in any pharmaceutically acceptable and effective dosage form. Examples of such dosage forms include (but are not limited to): intravenous, intramuscular, subcutaneous, intra-articular, intrasynovial, intrathecal, periostal, intratumoral, peritumoral, intralesional, perilesional, infusion, sublingual, bucal, transdermal, oral, topical or inhalation. Preferred dosage forms include oral, topical, intravenous, subcutaneous and transdermal.

In general, a therapeutically effective amount of a compound according to this invention is expected to vary in the range of about 0.1 mg/kg body weight/day (mg/kg/day) to about 100 mg/kg/day. Preferred amounts should range from about 0.1 mg/kg/day to about 50 mg/kg/day. More specifically, preferred dosage levels for various modes of administration are: intravenous (from about 0.1 mg/kg/day to about 40 mg/kg/day); intramuscular (from about 1 mg/kg/day to about 50 mg/kg/day); orally (from about 5 mg/kg/day to about 100 mg/kg/day); intranasal instillation (from about 5 mg/kg/day to about 100 mg/kg/day); and aerosol (from about 5 mg/kg/day to about 100 mg/kg/day).

Dosage forms may include any pharmaceutically acceptable carriers and adjuvants that are known to those of ordinary skill in the art. These carriers and adjuvants include, for example, ion exchangers, alumina, aluminum stearate, lecithin, serum proteins (such as human serum albumin), buffer substances (such as phosphates), glycine, sorbic acid, potassium sorbate, partial glyceride mixtures of saturated vegetable fatty acids, water, salts or electrolytes (such as protamine sulfate, disodium hydrogen phosphate, potassium hydrogen phosphate or sodium chloride), zinc salts, colloidal silica, magnesium trisilicate, polyvinyl pyrrolidone, cellulose-based substances and glycols (such as polyethylene glycol). Such forms include (but are not limited to) tablet, capsule, caplet, liquid, solution, suspension, emulsion, lozenges, syrup, reconstitutable powder, granule, suppository and transdermal patch. Methods for preparing such dosage forms are well known (see, for example, H. C. Ansel and N. G. Popovish, *Pharmaceutical Dosage Forms and Drug Delivery Systems,* 5th edition, Lea and Febiger, 1990).

The compounds of this invention may be administered alone or in combination with one or more conventional anti-neoplastic or anti-inflammatory agent. Such agents are well known and may be selected as circumstances dictate by those of ordinary skill in the art. Advantageously, such combination therapy may utilize lower dosages of the conventional therapeutic agents, thereby avoiding possible toxicity and adverse side effects incurred when those agents are administered as monotherapies. For example, the compounds of this invention may be used in combination with conventional cancer drugs (such as methotrexate, taxol, 5-fluorouracil, cis-platinum, cortisone, nitrogen mustards, thiotepa and nitrosoureas) and conventional anti-inflammatory drugs (such as non-steroidal anti-inflammatory agents, penicillamine, methotrexate, cortisone and gold salts).

Besides their therapeutic utility, the phosphotyrosine mimics of this invention may also be used to identify, isolate and purify regulatory proteins or fragments thereof that possess native phosphotyrosine-containing ligands or receptors. For example, it is possible to covalently link the phosphotyrosine mimics according to this invention (or compounds comprising them) to a solid support material, thereby creating an affinity chromatography matrix. Cell preparations may be passed through such a matrix to identify new tyrosine-kinase dependent regulatory proteins or alternatively, to isolate and purify known proteins. In many cases, phosphotyrosine (or a compound containing a phosphotyrosine residue) cannot be used for this purpose, given phosphotyrosine's strong polarity and tendency to hydrolyze. It will be clear to those of ordinary skill in the art that the generality and multiple utilities of the methods and kits described herein are unique and desirable features of this invention.

The following examples are provided to illustrate the invention described herein. These examples demonstrate various preferred embodiments of this invention and are not to be construed as limiting the scope of the invention in any way.

EXAMPLES

Example 1

ELISA for the Detection of Phosphotyrosine Mimics

A 96 well microtiter plate (Pierce #15126, Reacti-Bind Streptvidin coated polystyrene) was coated with 100 µl of biotinylated peptide ECQ(pY)QPQP (MW=1367.5) at a concentration of 15 nM in Tris Buffered Saline (TBST) (10 mM Tris.HCl, pH 7.5, 100 mM NaCl, 0.1% Tween 20) for 45 minutes at room temperature. The microtiter plate was washed 4 times with TBST. MAb PY-20 (Zymed #03-7799) was pre incubated for 45 minutes at a 2× concentration of 0.078 µg/ml (0.48 nm) with a 2× concentration of non-phosphorylated test compounds in TBST. 100 µl of test compound/antibody solution was added in duplicate to each of the wells and incubated at room temperature. The microtiter plate was washed 4 times with TBST. 100 µl of goat anti-mouse IgG (Heavy & Light chains F(ab')$_2$HRP) was added and diluted to 1:2000 in TBST. After incubating for 45 minutes at room temperature, the well were washed 4 times with TBST. 100 µl of enzyme substrate (Zymed #00-2011, ABTS Kit) was added as a buffer (9 parts dH$_2$O 'to 1 part 10× substrate buffer and 4 drops of 50× ABTS solution added just before use). After 20 minutes, the reaction was stopped by addition of 50 µl of stop solution. Optical density was measured at 405 nm. Phosphotyrosine mimics were detected by 50% or greater inhibition of anti-phosphotyrosine binding 15 µg/ml in the above assay.

Example 2

Synthesis of N-Boc-para-(2'-$^t$butoxycarbonylphenyl) phenylalanine

A Compound Containing a Functional Group-Protected Phosphotyrosine Mimic

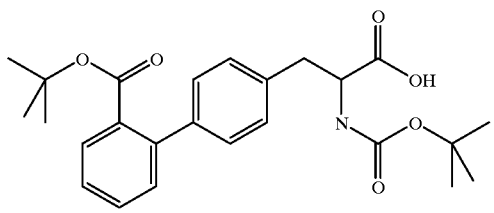

A. N-Boc-(para-tributylstannyl)phenylalanine-benzyl ester

A mixture of N-Boc-para-iodophenylalanine-benzyl ester (4.83 g), hexabutylditin (6.4 mL) and Pd(Ph$_3$P)$_2$Cl$_2$ (0.101 g) in dry toluene (70 mL) was heated at 60° C. under Argon for 55 hours. Aqueous potassium fluoride (20 mL, 1M solution) and tetrabutylammonium fluoride (1M in tetrahydrofuran, 1 mL) were added and the mixture was stirred at room temperature for 1 day. The mixture was diluted with ethyl acetate, washed with water, dried filtered and evaporated. The residue was fractionated over silica gel to give the N-Boc-(para-tributylstannyl)phenylalanine-benzyl ester (3.55 g).

B. N-Boc-para-(2'-$^t$butoxycarbonylphenyl)phenylalanine-benzyl ester.

A mixture of N-Boc-(para-tributylstannyl)phenylalanine-benzyl ester (0.661 g), 2-iodobenzoic acid $^t$butyl ester (0.334 g) and Pd(Ph$_3$P$_2$Cl$_2$) (0.035 g) in N-methylpyrrolidone (3 mL) was heated at 110° C. for 3 hours under argon. The mixture was diluted with ethyl acetate, washed with water, dried filtered and evaporated. The residue was fractionated over silica gel to give N-Boc-para-(2'-$^t$butoxycarbonylphenyl)phenylalanine-benzyl ester (0.203 g).

C. N-Boc-para-(2'-$^t$butoxycarbonylphenyl)phenylalanine.

A mixture of N-Boc-para-(2'-$^t$butoxycarbonylphenyl) phenylalanine-benzyl ester and 10% Palladium on charcoal (0.030 g) in ethanol 20 mL was hydrogenated at 35 psi for 23.5 hours. The reaction mixture was filtered through celite and evaporated to dryness to give the N-Boc-para-(2'-$^t$butoxycarbonylphenyl)phenylalanine (0.175 g).

Example 3

Representative Synthesis of Phosphotyrosine Mimic-Containing Peptide (BIRE0567)

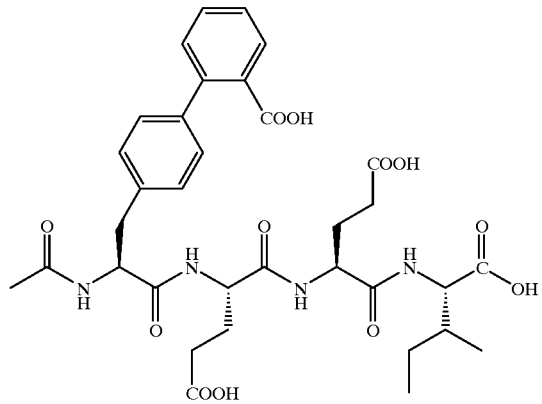

BIRE057

Peptide synthesis was carried out by solid-phase methodology using Fmoc-chemistry. The side chain protecting group was tert-butyl ester for Glu. The solid-phase used was Fmoc-L-Ile-HMPA resin (0.5 mmole/g). Coupling was carried out using 3 equivalents of the amino acid using the protocol amino acid:HBTU:HOBT:DIEA-1:1:1:2 molar ratios. Coupling times were typically 45 min. The same protocol was used to couple N-Boc-para-(2'-$^t$butoxycarbonylphenyl)phenylalanine. Cleavage of the peptide from the resin was achieved by treating the dried resin with trifluoroacetic acid:anisole:ethanedithiol:ethyl methyl sulfide-95:3:1:1 for 2 hrs at room temperature. The resin was filtered and washed with the cleavage cocktail. After evaporating trifluoroacetic acid under vacuum, the residue was treated with the cold diethyl ether. The precipitated solid was centrifuged off and the solid pellet obtained washed with ether, dissolved in aqueous acetonitrile and lyophilized.

N-terminal acetylation was carried out on the crude peptide in water at 0° C. for 45 min. using 5 equivalents of acetic anhydride. DIEA was to start the reaction at pH 7. Acetylated peptide was purified by reverse phase hplc on a Vydac C-18 preparative column (300 A° pore size, 10 mm particle size; 2.2 cm×25 cm) with UV monitoring at 215 nm and flow rate of 15 ml/min. The gradient conditions were 20–100%B over 25 min. Mobile phase A was 0.05% TFA/H$_2$O and B 60% acetonitrile/water containing 0.05% TFA. The major peak was collected and characterized by FABMS to give the desired M+.

While we have herein before presented a number of embodiments of this invention, it is apparent that our basic construction can be altered to provide other embodiments that utilize the processes and compositions of this invention. For example, obvious variations of the synthetic process steps and intermediates described and exemplified herein will be easily recognized by those of ordinary skill in the art. This application expressly envisions and extends to those obvious variations. It should be appreciated that the scope of this invention is defined by the following claims rather than by the specific embodiments that have been presented hereinabove by way of example.

We claim:

1. A method for identifying a phosphotyrosine mimic comprising the steps of:
   (a) providing a test compound and a phosphotyrosine containing substance;
   (b) contacting the compound and the phosphotyrosine containing substance with an anti-phosphotyrosine antibody; and
   (c) detecting by immunoassay the ability of the test compound to inhibit the binding of the anti-phosphotyrosine antibody to the phosphotyrosine-containing substance;
   wherein the phosphotyrosine containing substance and the test compound are capable of binding an anti-phosphotyrosine ant-body;
   and wherein the identified phosphotyrosine mimic is a phenyl carboxylic acid or a functional group protected derivative thereof, each being optionally substituted with a member selected from the group consisting of halogen, branched or unbranched $C_{1-5}$ alkyl, $C_{1-5}$ alkoxy, $C_{2-5}$ alkenyl, $C_{2-5}$ alkynyl, cyano, nitro, amino, trifluoromethyl, trifluoromethoxy and hydroxy; wherein any one of the foregoing alkyl, alkoxy, alkenyl or alkynyl groups is unsubstituted or substituted with cyano, nitro, amino, trifluoromethyl, trifluoromethoxy or hydroxy and wherein any unsubstituted methylene may be replaced with O, S or C=O.

2. The method according to claim 1, wherein said immunoassay is a competitive binding assay; and
   wherein said method further comprises detecting the degree to which the test compound displaces the phosphotyrosine-containing substance.

3. The method according to claim 2, wherein said method further comprises the steps of:
   (a) incubating the test compound with an anti-phosphotyrosine antibody to form a solution;
   (b) contacting the solution of step (a) with a known amount of a phosphotyrosine-containing substance; and
   detecting the degree to which the test compound displaces the phosphotyrosine-containing substance.

4. The method according to claim 1, wherein said method is an ELISA.

5. The method according to claim 4, wherein said anti-phosphotyrosine antibody is a monoclonal antibody.

6. The method according to claim 5, wherein said monoclonal antibody is PY-20.

7. The method according to claim 1 wherein said phosphotyrosine mimic is 2-phenyl carboxylic acid or a functional group protected derivative thereof.

* * * * *